United States Patent [19]

Hanson et al.

[11] Patent Number: 5,296,139
[45] Date of Patent: Mar. 22, 1994

[54] DIFFUSION CELL WITH FILTER SCREEN

[75] Inventors: William A. Hanson, Westlake Village; Steven W. Shaw, Thousand Oaks, both of Calif.

[73] Assignee: Hanson Research Corp., Chatsworth, Calif.

[21] Appl. No.: 76,965

[22] Filed: Jun. 16, 1993

[51] Int. Cl.$^5$ .............................................. B01D 65/08
[52] U.S. Cl. ...................... 210/297; 210/319; 210/321.63; 73/64.47
[58] Field of Search .............. 210/297, 299, 316, 319, 210/321.63, 321.84, 403, 415; 73/64.47; 366/273, 274

[56] References Cited

U.S. PATENT DOCUMENTS 4,594,884  6/1986  Bondi et al. .................... 210/321.84
5,198,109  3/1993  Hanson et al. .................. 210/321.75

Primary Examiner—Matthew O. Savage
Attorney, Agent, or Firm—Jack C. Munro

[57] ABSTRACT

A diffusion cell to facilitate the automated removal of test aliquots of liquid from a receptor chamber of the diffusion cell so as to determine percutaneous absorption through a membrane of a donor media from a donor chamber into the receptor chamber of the diffusion cell. There is utilized a sampling port through which the test aliquot is to be removed, the removal being achieved by means of a sample tube. Within the receptor chamber is located a stirring device in the form of a helical coil which is to be rotated to achieve stirring and homogeneous mixing of the liquid within the receptor chamber. Mounted within the coil is a filter screen to prevent particulate matter over a certain size from entering the sample tube and clogging such.

15 Claims, 1 Drawing Sheet

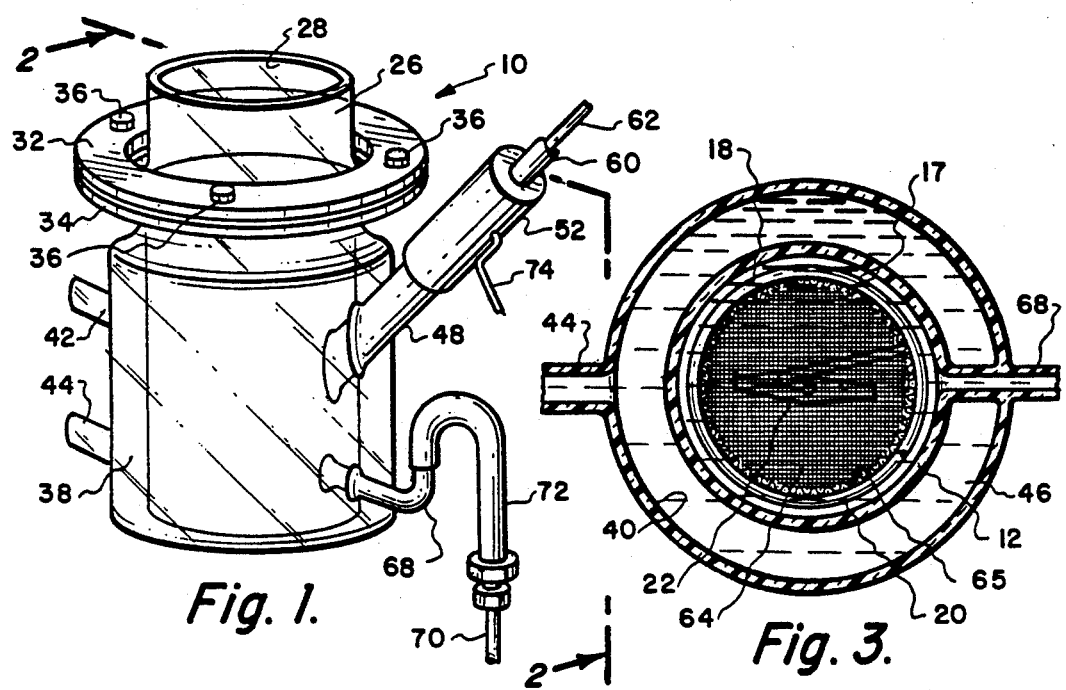
Fig. 1.
Fig. 3.
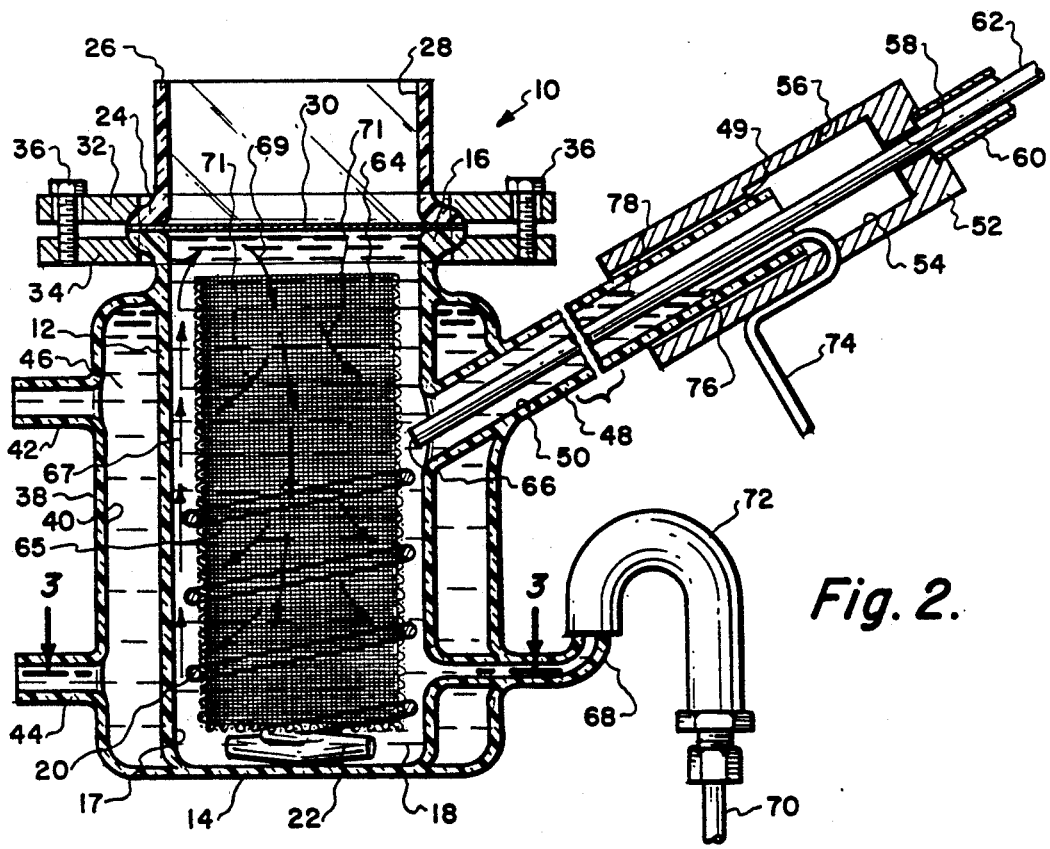
Fig. 2.

DIFFUSION CELL WITH FILTER SCREEN

BACKGROUND OF THE INVENTION

1) Field of the Invention

The field of this invention relates to testing equipment and more particularly to an apparatus which is usable to determine the transfer of a substance through a membrane into a liquid placed in contact with the opposite side of the membrane.

2) Description of the Prior Art

Percutaneous absorption test cells are used in the study of kinetics of the partition coefficients defining the passage and equilibrium states of components into and through a barrier separating two dissimilar substances. A typical test cell is known as the Franz cell. The Franz cell is in the form of a container with an upper half separated from a lower half by a porous membrane comprising a barrier. A clamping arrangement is located between the upper half of the lower half with the barrier in the form of a thin sheet of material to be placed and clamped tightly in a stretched configuration by a clamping arrangement.

The lower compartment of the Franz cell is completely filled with a receptor media in contact with the barrier. In the upper compartment there is placed a donor substance which may comprise a solid, semi-solid, gas or liquid. The receptor media normally comprises water, a buffered solution or a saline solution, but may consist of any polar or non-polar liquid, semi-liquid or gas with or without surfactants added. Connecting the lower compartment is a sample port and it is through this sample port that aliquots are to be removed. An aliquot is defined as an exact subvolume of the overall volume of the receptor media. A prior art type of diffusion cell has been obtained by the present inventor and carries U.S. Pat. No. 5,198,109, issued Mar. 30, 1993.

While generally useful in the whole field of physical chemistry, Franz cells have become particularly useful in the health care field. Levels of epidermal exposure to pesticides, chemicals, ointments and cosmetics are important in the field of environmental science. The rate of release and absorption of ingredients for medicinal skin patches is essential to determine the size, dosage amount and characteristics of the patch.

Within a Franz cell, typically the test is conducted by placing the donor substance against the total area of the barrier exposed to the upper compartment. A suitable receptor media, such as a saline solution, is placed in the lower compartment in contact with the barrier. Within this lower compartment is located a stirring device. The function of the stirring device is to homogeneously intermix the portion of the donor media that permeates the membrane into the receptor chamber.

The kinetics of membrane transfer involves more than the pore size of the membrane. Membranes have varying degrees of hydrophilic and hydrophobic characteristics. This is particularly true of skin. There are three layers of skin with varying characteristics in allowing the passage of fluids. While synthetic membranes are generally chosen for transfer studies with diffusion cells, natural skin, either human or animal, is used extensively within Franz cells.

Animal and human membranes may inadvertently release particulate matter into the receptor compartment. This particulate matter typically consists of organic integumentary particles of highly viscous aggregates ranging from diameters of one hundred microns to string-like particles of one thousand or more microns in length. Such particulates may clog the sample withdrawal tube and prevent consistent withdrawal rates particularly in an automated sampling system.

SUMMARY OF THE INVENTION

The diffusion cell of the present invention is in the form of a container which is divided between a bottom portion and a top portion. In between the bottom portion and the top portion is clamped a barrier formed of sheet material which is sufficiently porous to permit the transmission of a substance therethrough. Within the bottom portion is a receptor chamber which is to be filled with a receptor liquid. The top portion includes a donor chamber within which is to be located a donor media which is to be spread evenly across the barrier. Within the receptor chamber there is located a helical coil which is to be magnetically rotatably driven so as to function as a stirring apparatus. The length of the coil is at least one half the height of the receptor chamber. Connecting to the receptor chamber through the sidewall thereof is a sample port. Associated with the sample port is a sample tube with this sample tube to be movable to an inward position locating the sample tube within the receptor chamber to facilitate the removing of aliquots of the receptor media. Mounted within the helical coil stirring apparatus is a basket of mesh functioning as a filter. As liquid flows into the center of the basket and then out through the sidewall of the basket, any particulate matter larger than the mesh size of the basket will be caught by the basket and thus prevent it from entering the sample tube.

The primary objective of the present invention is to utilize a filter screen in conjunction with a diffusion cell so as to keep particulate matter from clogging a sample aliquot withdrawing tube.

Another objective of the present invention is to direct the liquid flow pattern within the receptor chamber in such a manner as to pass through the filter screen so as to capture any particulates on the inside of the filter screen with the sample tube being located exteriorly of the filter screen.

BRIEF DESCRIPTION OF THE DRAWING

FIG. 1 is an exterior isometric view of the diffusion cell of the present invention;

FIG. 2 is a cross-sectional view taken along a vertical plane through the diffusion cell of FIG. 1 and taken along line 2—2 of FIG. 1 showing the sample tube in the sample withdrawing position; and FIG. 3 is transverse cross-sectional view taken in the area of the refilling tube section of the diffusion cell of the present invention taken along line 3—3 of FIG. 2.

DETAILED DESCRIPTION OF THE SHOWN EMBODIMENT

Referring particularly to the drawing, there is shown in FIG. 1 the diffusion cell 10 of this invention. The diffusion cell 10 comprises a thin-walled cylindrical container 12 which has a closed bottom 14 and an open top defined by an outwardly flared annular flange 16. The container 12 has an internal chamber 17 which is to be filled with a receptor liquid 18. The receptor liquid 18 comprises a liquid such as water, saline or other similar type of solution.

Placed within the chamber 17 is a helical coil 20 which has a free upper end and at the lower end is attached to metallic elongated rod 22. Rod 22 is to be attracted to a magnet (not shown) which is to be located exteriorly of the container 10 and actually directly adjacent bottom 14. Rotation of this magnet will result in rotation of the rod 22 and simultaneous rotation of the coil 20. The coil 20 is of a length at least as great as one half the heigth of the chamber 17. It has been found that the stirring action caused by the coil 20 within the receptor liquid 18 is exceedingly effective and within a matter of just a few minutes will cause the liquid 18 to be homogeneous.

Abutting against the flange 16 is an annular flange 24 of a donor housing 26 which has an internal donor chamber 28. This chamber 28 is shown to be open at its upper end to the ambient. In some arrangements chamber 28 may be closed to ambient to prevent evaporation of donor contents. Tightly stretched across the width of the aligned chambers 17 and 28 is a thin sheet material barrier 30. This barrier 30 is fixedly held in position between the flanges 16 and 24 by means of a clamping mechanism in the form of a pair of plates 32 and 34. Interconnecting the plates 32 and 34 are a series of threaded fasteners in the form of bolts 36. Tightening of the bolts 36 will produce the clamping action tending to tightly clamp together the flanges 16 and 24.

Typical material for the barrier 30 can be any desired material. A desirable form of material for the barrier 30 would be a material that would essentially duplicate human skin. Although there are some plastics that do substantially duplicate human skin, the best barrier material would be human or animal skin. Also other types of synthetic material other than plastics could be utilized such as possibly a tightly woven cloth material.

It is desirable to have the receptor liquid 18 maintained at a specifically known temperature level. One convenient way to achieve this is by surrounding the container 12 with a jacket 38 which has an internal jacket chamber 40. Connecting with the chamber 40 is an inlet 44 and an outlet 42. A liquid 46 is to be supplied through the inlet 42 and caused to circulate within the chamber 40 and then exit through the outlet 42. With the liquid 46 being at a pre-established temperature, it can be readily seen that the receptor liquid 18 will be caused to quickly also assume that temperature.

Integrally connected to the wall of the container 12 is a sample port 48. This sample port 48 is open at its outer end and has an internal chamber 50. Fixedly mounted around the outer end of the sample port 48 is a cap 52. The cap 52 has an internal chamber 54 within which the open outer end of the sample port 48 is located. The cap 52 is fixed onto the exterior surface of the sample port 48 by a plurality of spacer blocks 49. The cap 52 may include a hole 56 so that ambient air pressure can be applied against the liquid 18 at the level 78 shown within FIGS. 2 and 3 of the drawing. This level 78 of the liquid 18 is in alignment with the barrier 30 since the liquid 18 must be in contact with the barrier 30.

The outer end of the cap 52 includes a hole 58. Fixedly mounted to the exterior wall surface of the cap 52 around the hole 58 is a guide tube 60. Movably mounted within the guide tube 60 and extending through the hole 58 is a sample tube 62. The sample tube 62 has an internal passage (not shown). This sample tube 62 has an inner end 66.

The sample tube 62 is to be movable within the guide tube 60 so that the end 66 can be located in the sample-taking position as shown in FIG. 2 in the internal chamber 17. This sample tube 62 can be positioned in a retracted position spaced exteriorly of the liquid 18 which is not shown. With the tube 62 in the position shown in FIG. 2, a known quantity of the liquid 18 is to flow through the sample tube 62 to then be deposited to the appropriate collecting container (not shown). Normally, the quantity of aliquot extracted through the sample tube 62 comprises several hundred microliters.

If the volume of the aliquot is substantial, it would be possible to lower the level of the liquid 18 so that air bubbles would be caused to enter the chamber 17 and come to rest against the lower surface of the barrier 30. This is to be prevented and, in order to absolutely prevent this, it is desirable to simultaneously refill the chamber 17 with new liquid as the aliquot is removed by the sample tube 62. However, it is important that the new liquid that is being supplied does not mix with the portion of the liquid that is being extracted through the sample tube 62. In order to achieve this end result, a refilling port 68 is integrally connected to the wall of the container 12 with this refilling port 68 being located directly adjacent the bottom 14 and spaced some distance from the inner end 66 of the tube 62 during the time that this aliquot is being taken. Fresh new liquid is to be supplied from a source (not shown) through supply tube 70, hose 72 into refilling port 68 and hence into the chamber 17.

It is normally designed for the refilling liquid be supplied to the refilling port 68 to be of the precise same volume of the aliquot that is being withdrawn by the sample tube 62. If, per chance, a slightly greater amount of liquid is supplied through the refilling tube 68, there will be a certain amount of excess that would be created. Mounted within the internal chamber 50 of the sample port 48 is an overflow or leveling tube 74 with this overflow tube 74 terminating in an inner end 76. This inner end 76 is to be positioned precisely at the surface 78 of the liquid within the internal chamber 50 of the sample tube 48. The height of the surface 78 is to be at the same horizontal plane as the barrier 30. Therefore, any excess liquid 18 would be caused to flow through the overflow tube 74 and be extracted. In actual practice, a vacuum may be supplied continuously to the overflow tube 74 in order to facilitate the removal of this excess. Also, a pump is to be connected with the conduit 70, which is not shown, with this pump functioning to add under pressure the refilling fresh portion of the liquid.

Placed inside of the helical coil 20 is a basket 64. The basket 64 is to be placed directly against the interior surface 65 of the coil 20. This inside surface 65 takes the form of a cylinder. Although it is not absolutely necessary that the basket 64 be cylindrical, it is normally preferred. It also is generally preferable that the basket 64 actually rest against the surface 65 and again although it may not be attached to coil 65 it is generally preferred that it does do so. Since the coil 65 is adapted to rotate, then the basket 64 will also rotate with the coil 20.

The basket 64 is to be constructed of any suitable material such as stainless steel or plastic. The basket 64 has a mesh in the range of twenty to eighty per inch producing an approximate porosity of one hundred and eighty to eight hundred an sixty microns square. Coil 20 has a pitch and is rotated in the direction to drive the receptor media 18 in the direction of arrows 67 in the space between the coil 20 and the wall surface of the receptor chamber 17. The receptor media is then caused to flow against the barrier 30 and down into the center of the receptor chamber 17 and also within the center of the basket 64. This downward direction is depicted by arrows 69. Particulates will be retained on the inner circumfrence of the filter basket 64 and are therefore not in a position to clog the sample tube 62. Most of the liquid that is contained within the basket 64 will flow through the sidewall of the basket 64 as is represented by arrows 71.

It is to be understood that it is possible for the basket 64 to be spaced from the surface 65 although it is envisioned that that would not be preferable. It is also to be noticed that the basket 64 is to be constructed substantially the length of the receptor chamber 17 with only a slight space being located from the basket 64 to the barrier 30 and a slight space located from the basket 64 to the bottom 14. However, again, the length of the basket 64 could be shortened if such was deemed to be desirable. It is important, however, for the basket 64 to be located across the inner end 66 of the sample tube 62. Inherently, there will be a sucking or drawing action by the tube 62 when extracting an aliquot. This means that the receptor liquid 18 will be drawn right through the basket 64 prior to moving within the tube 62. Therefore, the basket 64 will remove any particulate matter of a sufficient size that could possibly clog the tube 62.

What is claimed is:

1. A diffusion cell comprising:
a chamber divided by a membrane into a donor chamber and a receptor chamber, a liquid filling said receptor chamber and being in contact with said membrane, a media supplied into said donor chamber with said media being permitted to diffuse through said membrane and be mixed with said liquid; and
said receptor chamber including a mixing device, said mixing device to be operated to affect eve mixing of said liquid within said receptor chamber, said mixing device comprising a helical coil of a length equal to at least one half the length of said receptor chamber, means for rotating said coil about a longitudinal axis thereof, said helical coil defining an interior surface, a filter screen located within said coil, said filter screen being located directly adjacent said interior surface substantially covering said interior surface, said filter screen forming a basket having an open end spaced from and adjacent to said membrane.

2. The diffusion cell as defined in claim 1 wherein:
said filter screen being tubular.

3. The diffusion cell as defined in claim 2 wherein:
said filter screen being cylindrical.

4. The diffusion cell as defined in claim 1 wherein:
said filter screen being substantially the length of said receptor chamber.

5. The diffusion cell as defined in claim 1 wherein:
said filter screen is mounted on said coil and being rotatable therewith.

6. The diffusion cell as defined in claim 5 wherein:
said means for rotating includes a magnetizable member adapted to be moved by a magnet located exteriorly of said receptor chamber.

7. The diffusion cell as defined in claim 1 wherein:
a sample port connecting with said receptor chamber, said sample port permitting removal of a quantity of said liquid.

8. The diffusion cell as defined in claim 7 wherein:
a refilling port connecting with said receptor chamber, said refilling port permitting supplying of an additional quantity of said liquid into said receptor chamber.

9. The diffusion cell as defined in claim 8 wherein:
said donor chamber is positionable at a higher elevation than said receptor chamber.

10. The diffusion cell as defined in claim 9 wherein:
said sample port connecting with said receptor chamber inbetween said refilling port and said membrane.

11. The diffusion cell as defined in claim 10 wherein:
said filter screen being tubular.

12. The diffusion cell as defined in claim 11 wherein:
said filter screen being cylindrical.

13. The diffusion cell as defined in claim 12 wherein:
said filter screen being substantially the length of said receptor chamber.

14. The diffusion cell as defined in claim 13 wherein:
said filter screen is mounted on said coil and being rotatable therewith.

15. The diffusion cell as defined in claim 14 wherein:
said means for rotating includes a magnetizable member adapted to be moved by a magnet located exteriorly of said receptor chamber.

* * * * *